United States Patent [19]

Schwalbach

[11] Patent Number: 5,018,967
[45] Date of Patent: May 28, 1991

[54] DENTAL FLUORIDE APPLICATOR AND METHOD FOR USING SAME

[76] Inventor: Stephen Schwalbach, 1966 Golf View Dr., River Falls, Wis. 54022

[21] Appl. No.: 567,611

[22] Filed: Aug. 15, 1990

[51] Int. Cl.$^5$ ............................................. A61C 9/00
[52] U.S. Cl. ...................................... 433/37; 433/91; 433/94; 433/215; 433/217.1
[58] Field of Search ...................... 433/37, 48, 91, 94, 433/217.1, 215

[56] References Cited

U.S. PATENT DOCUMENTS

| | | | |
|---|---|---|---|
| 603,803 | 5/1898 | White | 433/37 |
| 1,611,152 | 12/1926 | Backus | 433/47 |
| 1,986,275 | 1/1935 | Lowry | 433/93 |
| 2,311,158 | 2/1943 | Conway et al. | 433/36 |
| 2,701,916 | 2/1955 | Jarboe | 433/96 |
| 2,776,486 | 1/1957 | Manczur | 433/35 |
| 3,060,935 | 10/1962 | Riddell | 433/217.1 X |
| 3,468,029 | 9/1969 | Moore | 433/38 |
| 3,527,219 | 9/1970 | Greenberg | 433/215 X |
| 3,688,406 | 9/1972 | Porter et al. | 433/80 X |
| 3,722,097 | 3/1973 | Colman et al. | 433/36 |
| 3,772,790 | 11/1973 | Swan-Gett | 433/136 |
| 4,138,814 | 2/1979 | Weitzman | 433/215 |
| 4,382,785 | 5/1983 | Lococo | 433/36 |
| 4,417,874 | 11/1983 | Andersson et al. | 433/96 |
| 4,445,856 | 5/1984 | Sturtzkopf | 433/71 |
| 4,531,914 | 7/1985 | Spinello | 433/48 |
| 4,652,237 | 3/1987 | Cills | 433/37 |
| 4,695,253 | 9/1987 | Tysse | 433/136 |

FOREIGN PATENT DOCUMENTS 2481107 10/1981 France ...................... 433/215

*Primary Examiner*—John J. Wilson
*Assistant Examiner*—Jeffrey A. Smith
*Attorney, Agent, or Firm*—Finnegan, Henderson, Farabow, Garrett & Dunner

[57] ABSTRACT

A method and apparatus for applying fluoride to the teeth of a patient. The apparatus includes a dental tray, which is sized and shaped to fit between the upper and lower sets of the patient's teeth. The dental tray is preferably a unitary block of a disposable, deformable material, having a top surface and a bottom surface into which simultaneous dental impressions of the upper and lower sets of teeth are to be made. The side wall of the dental tray includes a groove, which extends around the perimeter of the dental tray. The apparatus further includes an evacuation tube. The evacuation tube has a first end which is adapted to communicate with a source of suction, such as a saliva ejector. The remainder of the evacuation tube has a plurality of apertures which serve as entry ports through which displaced fluoride solution, saliva and other debris are aspirated. The first end of the evacuation tube is disposed near the front of the dental tray, and the remainder of the tube is frictionally mounted within the groove of the dental tray. In use, the apparatus is inserted into the mouth of the patient, and impressions of the upper and lower sets of teeth are made in the top and bottom surfaces, respectively. An appropriate amount of fluoride solution is painted onto the impressions, the evacuation tube is connected to a saliva ejector, and the apparatus is reinserted into the patient's mouth.

13 Claims, 4 Drawing Sheets

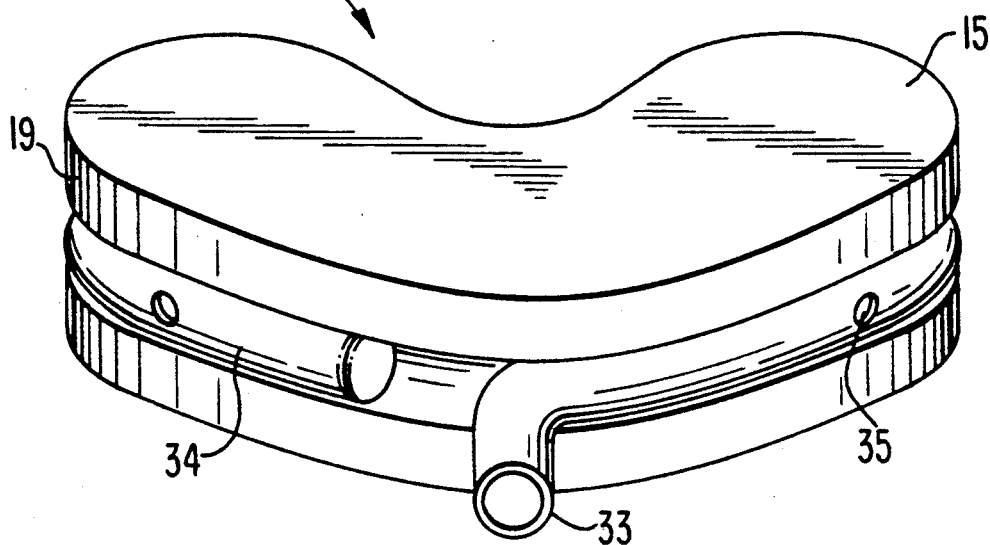
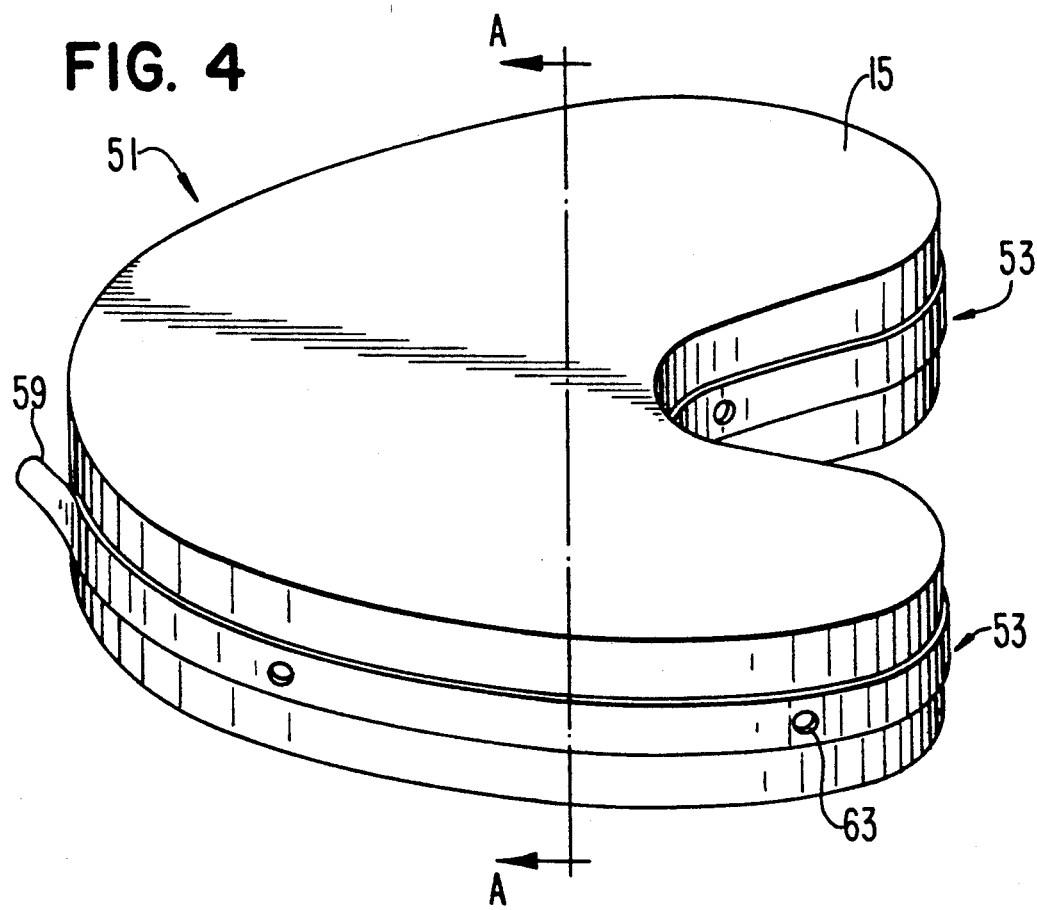

DENTAL FLUORIDE APPLICATOR AND METHOD FOR USING SAME

BACKGROUND OF THE INVENTION

1. Field of the Invention

The present invention relates generally to dental tools, appliances, and the like and, more particularly, to a method and apparatus for applying fluoride to the teeth of a patient.

2. Description of Related Art

The benefits associated with the treatment of teeth with fluoride have long been recognized. Unfortunately, however, fluoride treatments, as currently administered by dentists, are frequently unpleasant experiences for patients. The typical method by which dentists administer fluoride to patients is as follows: Two dental trays, each in the form of a U-shaped trough and each made of a non-deformable material, are coated on their inner surfaces with a syrupy solution containing fluoride. Both trays are then inserted into the mouth of the patient, one tray for the upper set of teeth, the other tray for the lower set of teeth. The patient then bites into the fluoride-covered trays, i.e. inserts his teeth into the trough-shaped trays, and allows the fluoride solution to coat his teeth for the necessary period of time.

One problem with the foregoing method is that, by biting into the fluoride-covered trays, the patient displaces some of the fluoride solution from the dental trays into his mouth. This is undesirable as most patients do not wish to have the fluoride solution in their mouths, where it can accidentally be swallowed. Therefore, to remove the displaced fluoride solution from the patient's mouth, the dentist typically places an evacuation tube (which is connected at one end to a source of suction) into the patient's mouth between the two dental trays. In addition to removing the displaced fluoride solution, the evacuation tube is also used to withdraw saliva and other debris from the patient's mouth which may make the patient uncomfortable.

This approach, however, is not entirely satisfactory because the evacuation tube, by virtue of being physically constrained to the area between the two dental trays, is unable to withdraw from the patient's mouth much of the displaced fluoride solution, saliva and other debris that accumulates in the area around the patient's teeth, gums, and cheeks. Another problem with the above-described technique is that it involves placing two, rather bulky, dental trays and an evacuation tube in the patient's mouth. For obvious reasons, this can be quite uncomfortable to the patient.

SUMMARY OF THE INVENTION

Accordingly, it is an object of the present invention to provide a method and apparatus for applying fluoride to the teeth of a patient which is more comfortable to the patient than existing methods and apparatuses.

It is a feature of the present invention to use a single dental tray having a deformable top region and a deformable bottom region into which simultaneous impressions of the upper and lower sets of teeth, respectively, may be made.

It is, therefore, an advantage of the present invention that the single dental tray of the present invention occupies less space in the patient's mouth than the two dental trays previously used.

It is another feature of the present invention to have an evacuation tube, having a plurality of apertures spaced along the length thereof, mounted along the periphery of the side wall of the dental tray.

It is, therefore, an advantage of the present invention that displaced fluoride, saliva and other debris may be withdrawn from heretofore inaccessible regions of the patient's mouth.

It is still another feature of the present invention that the method of applying the fluoride solution to the patient's teeth comprises having the patient make a dental impression in the tray by biting into it with his top and bottom teeth and then applying fluoride solution to the dental impression.

It is, therefore, an advantage of the present invention that the fluoride-coated dental tray is "custom-fitted" to the patient's mouth so that when the tray is reinserted into the patient's mouth and the patient bites into the dental tray, less fluoride solution is displaced from the dental tray.

Additional objects, features and advantages of the present invention will be set forth in part in the description which follows, and in part will be obvious from the description or may be learned by practice of the invention. The objects, features and advantages of the invention may be realized and attained by means of the instrumentalities and combinations particularly pointed out in the appended claims.

To achieve the foregoing objects and in accordance with the purpose of the invention, as embodied and broadly described herein, an apparatus for use in applying fluoride to the teeth of a patient comprises a dental tray, the dental tray having a top surface and a bottom surface, the top surface and the bottom surface being made of deformable material suitable for the making of a dental impression therein, the apparatus further comprising an evacuation tube, the evacuation tube having a first end adapted for communication with a source of suction, the remainder of the evacuation tube having a plurality of apertures spaced along the length thereof for aspirating materials therethrough, the remainder of the evacuation tube being mounted along the periphery of the dental tray.

Additionally, to achieve the foregoing objects and in accordance with the purpose of the invention, as embodied and broadly described herein, a method of applying fluoride to the teeth of a patient comprises the steps of inserting into the mouth of the patient an apparatus comprising a dental tray, the dental tray having a top surface and a bottom surface, the top surface and the bottom surface being made of deformable material suitable for the making of a dental impression therein, the apparatus further comprising an evacuation tube, the evacuation tube having a first end adapted for communication with a source of suction, the remainder of the evacuation tube having a plurality of apertures spaced along the length thereof for aspirating materials therethrough, the remainder of the evacuation tube being mounted along the periphery of the dental tray, then, closing the mouth of the patient so that impressions of the upper and lower sets of teeth of the patient are simultaneously formed in the top and bottom surfaces, respectively, of the dental tray, then, removing the apparatus from the mouth of the patient, then, applying fluoride to the impressions in the top and bottom surfaces of the dental tray, connecting the first end of the evacuation tube to a source of suction, reinserting the apparatus into the mouth of the patient, positioning the apparatus so that the impressions are aligned with the teeth of the patient, then, closing the mouth of the patient so that his teeth fill the impressions and become completely immersed in the fluoride solution, and then, after waiting an effective amount of time, removing said apparatus from the mouth of the patient.

The accompanying drawings, which are hereby incorporated in and constitute a part of this Specification, illustrate the preferred embodiments of the invention and, together with the description, serve to explain the principles of the invention.

BRIEF DESCRIPTION OF THE DRAWINGS

In the drawings wherein like reference numerals represent like parts:

FIG. 3 is a front perspective view of the apparatus shown in FIG. 1;

FIG. 4 is a perspective view, taken from the top right, of another embodiment of an apparatus for use in applying fluoride to the teeth of a patient, the apparatus being constructed according to the teachings of the present invention;

DETAILED DESCRIPTION OF PREFERRED EMBODIMENTS

The present invention is directed to a new and improved method and apparatus for applying fluoride to the teeth of a patient. The method and apparatus of the present invention provide the patient with a more comfortable fluoride treatment than is presently available. To achieve this effect, the present invention provides a dental tray which can be used to apply flouride simultaneously to the patient's upper and lower teeth. In addition, the present invention provides that the patient make an impression of both sets of teeth in the dental tray and that the fluoride solution be applied to those impressions. In this way, the tray is "custom-fitted" to the patient so that when the patient bites again into the tray, the fluoride solution conforms to the surface of the patient's teeth, and as a result, less fluoride solution is displaced from the tray. The present invention also provides an evacuation tube which is mounted to the periphery of the dental tray and which is used to withdraw fluoride solution, saliva and other debris from the patient's mouth.

Figure 1:
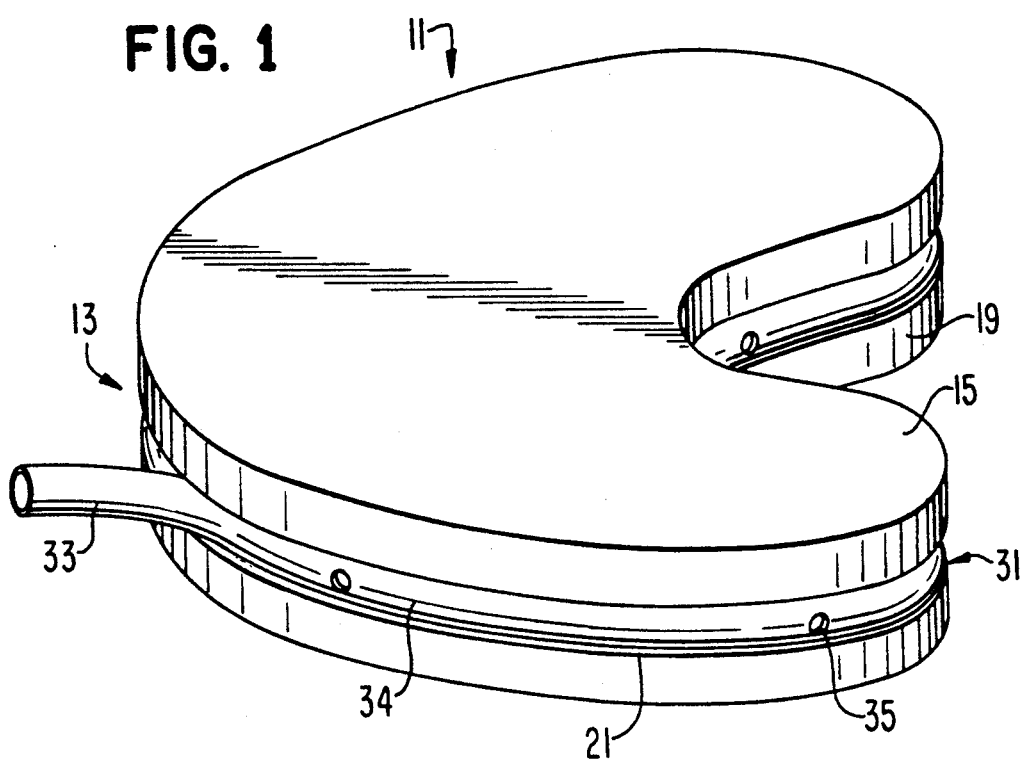
FIG. 1 is a perspective view, taken from the top right, of one embodiment of an apparatus for use in applying fluoride to the teeth of a patient, the apparatus being constructed according to the teachings of the present invention.
Figure 2:
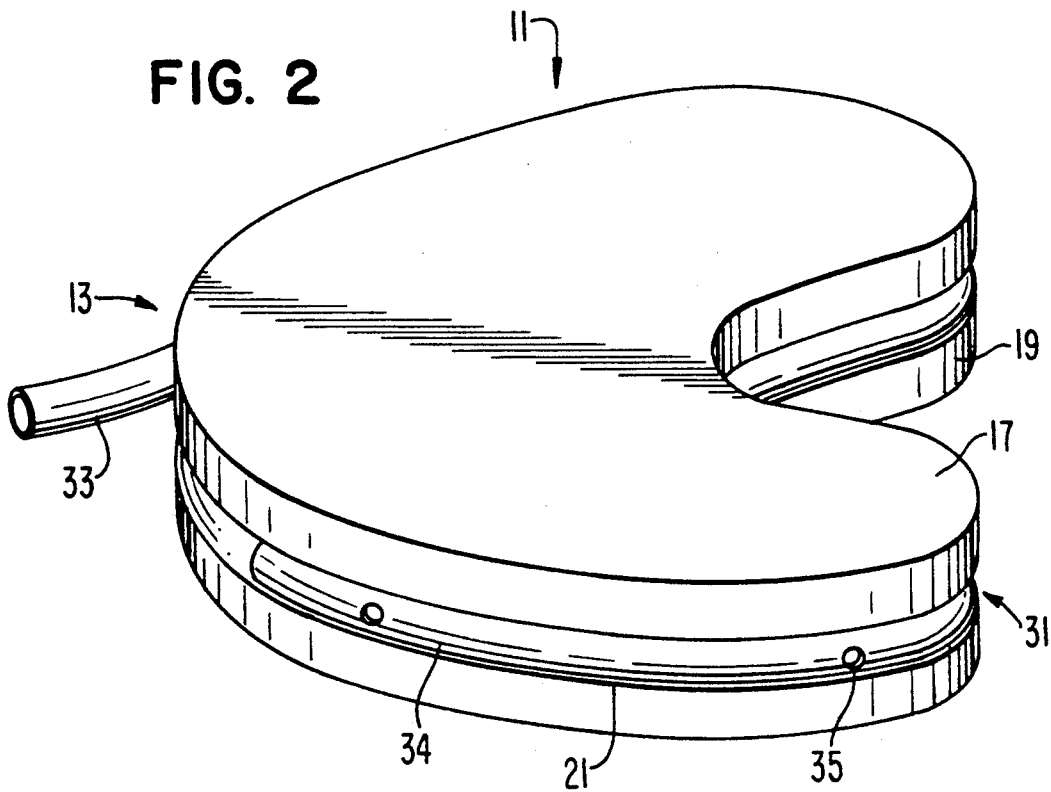
FIG. 2 is a perspective view, taken from the bottom right, of the apparatus shown in FIG. 1.
Figure 5:
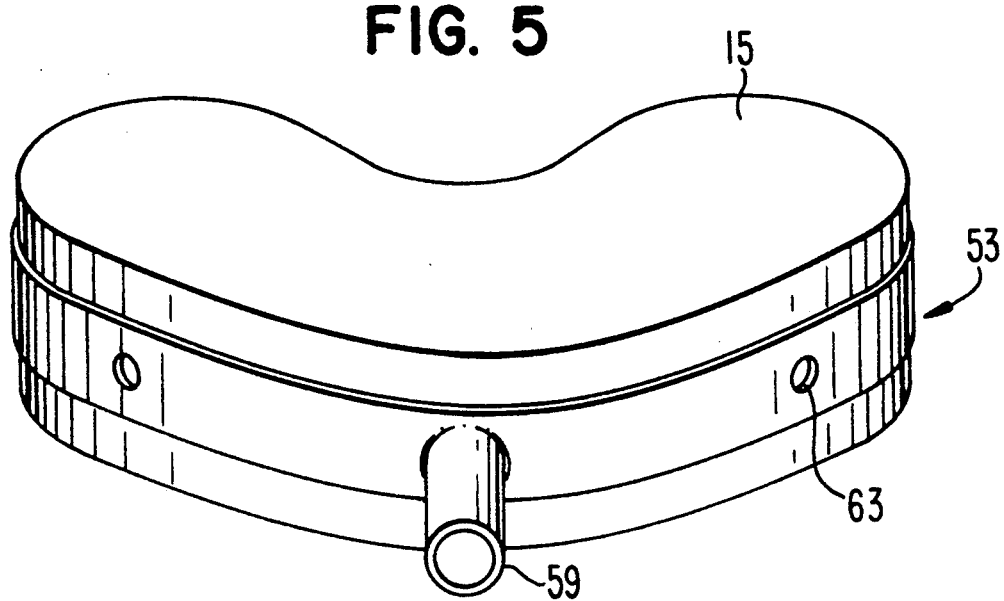
FIG. 5 is a front perspective view of the apparatus shown in FIG. 4.
Figure 6:
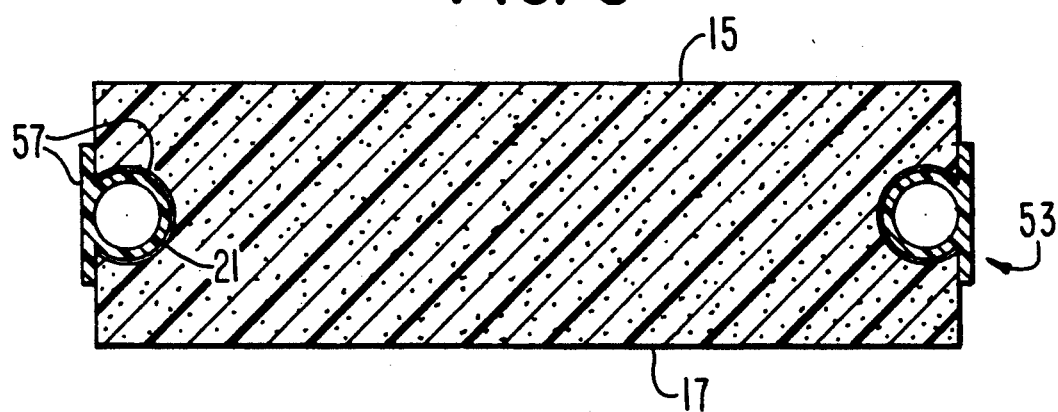
FIG. 6 is a section view taken along line A—A of FIG. 4.
Figure 7:
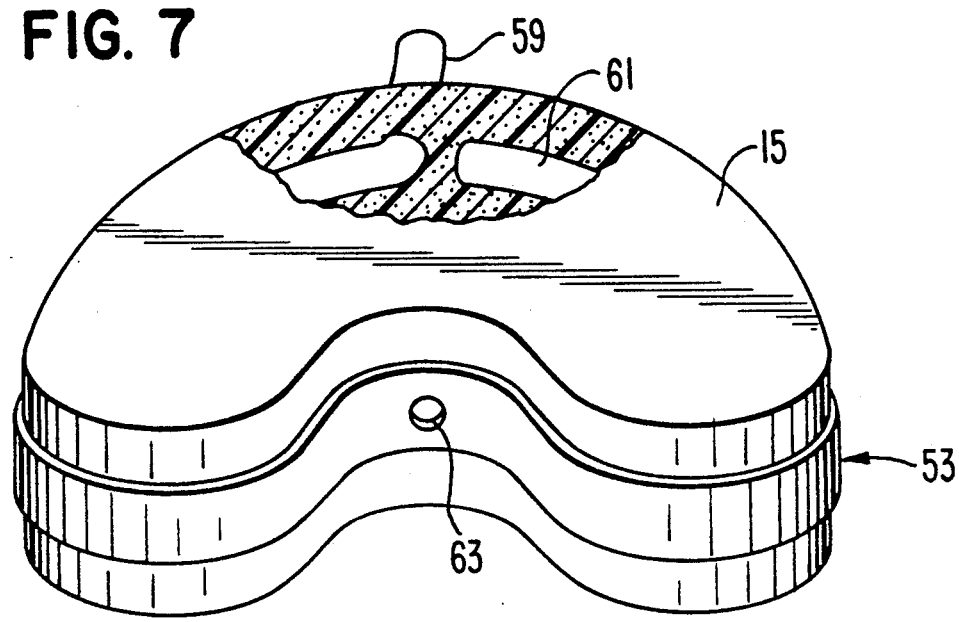
FIG. 7 is a back perspective view of the apparatus of FIG. 4, the figure being broken away in part to reveal a portion of the evacuation tube formed in the frame.

Referring now to the drawings and particularly to FIGS. 1 through 3, there is illustrated one embodiment of an apparatus for use in applying fluoride to the teeth of a patient, the apparatus being constructed according to the teachings of the present invention and being designated generally by reference numeral 11.

Apparatus 11 includes a dental tray 13. Dental tray 13 is appropriately sized and shaped to fit in a patient's mouth between the upper and lower sets of teeth. For example, the rear portion of dental tray 13 is preferably shaped to accommodate the tongue of the patient and to avoid contact of the dental tray with the soft palate of the patient (to prevent initiation of the gag reflex). Also, the thickness of dental tray 13 preferably varies, depending on the size of the mouth of the patient being treated. For example, the thickness of dental tray 13 for a small child is preferably approximately 10 mm whereas the thickness of dental tray 13 for a large adult is preferably approximately 16 mm.

Dental tray 13 is preferably a unitary structure, made of a disposable, deformable, molded material, such as Styrofoam TM expanded cellular polystyrene or the like. Dental tray 13 includes a top surface 15 for use in making an impression of the patient's upper set of teeth, a bottom surface 17 for use in making an impression of the patient's lower set of teeth, and a side wall 19, which extends from top surface 15 to bottom surface 17 around the perimeter of dental tray 13. Side wall 19 includes a peripherally-extending groove 21 whose purpose will be discussed below.

Apparatus 11 further includes an evacuation tube 31. Evacuation tube 31 is an elongated (i.e., slightly longer than the perimeter of dental tray 13) piece of tubing of the type typically used by dentists to aspirate materials, such as saliva, from a patient's mouth. Preferably, evacuation tube 31 has a diameter and rigidity approximating that of a cocktail straw. Evacuation tube 31 has a first end 33 which extends away from (e.g. by approximately one inch) the front end of tray 13 and which is adapted for communication with a source of suction, such as a saliva ejector. The remainder 34 of evacuation tube 31 is frictionally mounted within groove 21 and extends along the periphery of tray 13. Remainder 34 includes a plurality of apertures 35 (preferably approximately five apertures which are disposed as in FIGS. 1-3) which are spaced along the length thereof. Apertures 35 provide entry ports through which displaced fluoride, saliva and debris may be aspirated.

Referring now to FIGS. 4 through 7, there is illustrated another embodiment of an apparatus for applying fluoride to the teeth of a patient, the apparatus being constructed according to the teachings of present invention and being represented by the reference numeral 51.

Apparatus 51, like apparatus 11, includes a dental tray 13 made of deformable material, tray 13 being defined by a top surface 15, a bottom surface 17, a side wall 19, and a peripherally-extending groove 21.

Apparatus 51 further comprises a frame 53, which extends along the periphery of side wall 19. Frame 53 is preferably a unitary structure, and more preferably, is a unitary structure that is molded from a rigid plastic, metal or other similar material. Frame 53 serves two principle functions: First, it prevents tray 13 from expanding laterally when the patient bites into surfaces 15 and 17. Second, it is shaped to define an evacuation tube 57 which is used to withdraw any displaced fluoride or other debris from the patient's mouth. Evacuation tube 57 includes a first end 59 which is adapted to communicate with a source of suction. First end 59 also extends outward from the front of frame 53 for a short distance (approximately one inch). The remainder 61 of evacuation tube 57, which is formed along the inner surface of frame 53, is disposed along the periphery of tray 13, being frictionally mounted within groove 21. The diameter of remainder 61 preferably approximates that of a cocktail straw. A plurality of apertures 63 (preferably approximately five apertures, which are disposed as in FIGS. 4–7) which serve as ports of entry into tube 57 for the fluoride solution and debris, are spaced along the length of the outer surface of frame 53 so as to be in communication with remainder 61.

To use apparatus 11 (or apparatus 51) to apply fluoride to the teeth of a patient, one inserts the apparatus into the patient's mouth and causes impressions of the upper and lower sets of teeth of the patient to be made in top surface 15 and bottom surface 17, respectively. Next, the apparatus is removed from the mouth of the patient, and fluoride solution is applied to (i.e., painted onto) the impressions formed in the top and bottom surfaces. Preferably, the amount of fluoride solution that is painted onto the impressions is just enough so that when the patient's teeth are reinserted into the impressions, the fluoride solution conforms to the surface of the patient's teeth but does not become displaced from the dental tray. With the fluoride solution so applied to the impressions, the first end of the evacuation tube is then connected to a saliva ejector or other source of suction. (Connection of the evacuation tube to a source of suction may also take place after the apparatus is reinserted into the patient's mouth.) The apparatus is then reinserted into the mouth of the patient and positioned so that the impressions are aligned with the patient's teeth. The patient then bites again into the dental tray, causing the fluoride solution in the impression to conform to the shape of his teeth. Any fluoride solution that is displaced into the patient's mouth, as well as any saliva or debris that are present therein, enter the evacuation tube and are withdrawn. When the treatment is complete, the apparatus is removed from the patient's mouth.

Figure 8:
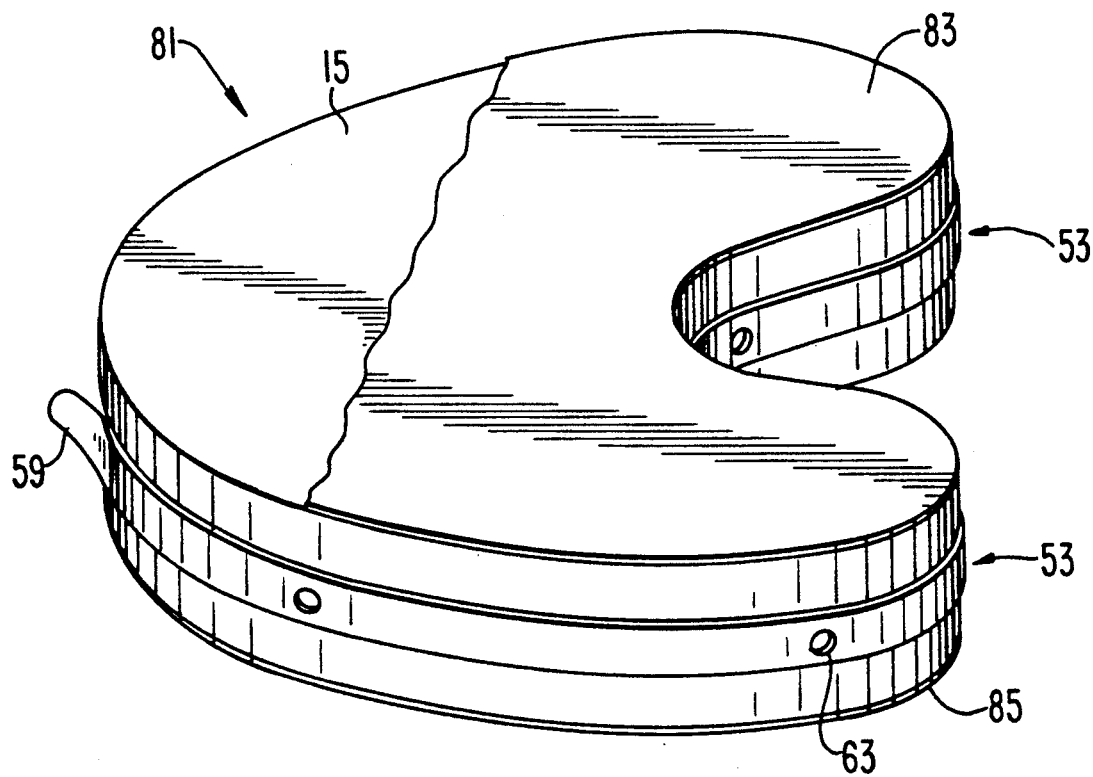
FIG. 8 is a perspective view, taken from the top right and broken away in part, of still another embodiment of an apparatus for use in applying fluoride to the teeth of a patient, the apparatus being constructed according to the teachings of the present invention.

Referring now to FIG. 8, there is illustrated still another embodiment of an apparatus for applying fluoride to the teeth of a patient, the apparatus being constructed according to the teachings of present invention and being represented by the reference numeral 81.

Apparatus 81 is similar in construction to apparatus 51, except that apparatus 81 further comprises a pair of liners 83 and 85, which are detachably mounted on top surface 15 and bottom surface 17, respectively. Preferably, liners 83 and 85 are made of paper or a similarly suitable material and include a self-adhesive material that permits the liners to be easily attached to and removed from surfaces 15 and 17. The purpose of liners 83 and 85 is to cause a greater deformation of dental tray 13 (i.e., a deeper impression in dental tray 13) when a patient bites thereinto. With a deeper impression, one may apply more fluoride solution.

Apparatus 81 is used in the same manner as apparatuses 11 and 51, except that liners 83 and 85 are removed from tray 13 after the making of the dental impression and before the application of the fluoride solution.

It is to be understood that the above-described liners may also be used in the same manner with other apparatuses constructed according to the teachings of the present invention, such as apparatus 11.

Although the present invention has been described in connection with preferred embodiments, it is understood that those skilled in the art are capable of making modifications and variations without departing from the scope or spirit of the present invention. Therefore, the foregoing description of preferred embodiments is not to be taken in a limiting sense, and the present invention is best defined by the following claims and their equivalents.

What is claimed is:

1. An apparatus for use in applying fluoride to the teeth of a patient, comprising:
   a) a dental tray, said dental tray having a top surface being made of deformable material suitable for the making of a dental impression therein; and
   b) an evacuation tube, said evacuation tube having a first end adapted for communication with a source of suction, the remainder of said evacuation tube having a plurality of apertures spaced along the length thereof for aspirating materials therethrough, said remainder of said evacuation tube being mounted along the periphery of said dental tray.

2. The apparatus of claim 1 wherein said dental tray has a side wall which extends from said top surface to said bottom surface and wherein said side wall has a peripherally-extending groove into which said remainder of said evacuation tube is frictionally mounted.

3. The apparatus of claim 2 wherein said dental tray is a unitary block of disposable, deformable material.

4. The apparatus of claim 3 wherein said dental tray is made of expanded cellular polystyrene.

5. An apparatus for applying fluoride to the teeth of a patient, comprising:
   a) a dental tray, said dental tray having a top surface and a bottom surface, said top surface and said bottom surface being made of deformable material suitable for the making of an impression therein, said dental tray further having a side wall which extends from said top surface to said bottom surface, said side wall having a peripherally-extending groove; and
   b) a frame mounted against said side wall, said frame having an evacuation tube formed therein, said evacuation tube having a first end adapted for communication with a source of suction, the remainder of said evacuation tube having a plurality of apertures spaced along the length thereof for aspirating materials therethrough, said remainder of said evacuation tube being disposed within said groove of said dental tray.

6. The apparatus of claim 5, further comprising a first liner detachably mounted on said top surface and a second liner detachably mounted on said bottom surface.

7. A method of applying fluoride to the teeth of a patient, comprising the steps of:
   a) inserting into the mouth of the patient an apparatus comprising a dental tray, said dental tray having a top surface and a bottom surface, said top surface and said bottom surface being made of deformable material suitable for the making of a dental impression therein, and further comprising an evacuation tube, said evacuation tube having a first end adapted for communication with a source of suction, the remainder of said evacuation tube having a plurality of apertures spaced along the length thereof for aspirating materials therethrough, said remainder of said evacuation tube being mounted along the periphery of said dental tray;
   b) then, closing the mouth of the patient so that impressions of the upper and lower sets of teeth of the patient are simultaneously formed in said top surface and said bottom surface of said dental tray;

c) then, removing said apparatus from the mouth of the patient;

d) then, applying an appropriate amount of fluoride solution to the impressions in said top surface and said bottom surface of said dental tray;

e) connecting said first end of said evacuation tube to a source of suction;

f) reinserting said apparatus into the mouth of the patient, positioning said apparatus so that the impressions are aligned with the teeth of the patient;

g) then, closing the mouth of the patient so that the teeth fill the impressions and become completely immersed in the fluoride solution; and h) then, after waiting an effective amount of time, removing said apparatus from the mouth of the patient.

8. The method of claim 7 wherein said dental tray has a side wall which extends from said top surface to said bottom surface and wherein said side wall has a peripherally-extending groove into which said remainder of said evacuation tube is frictionally mounted.

9. The method of claim 8 wherein said dental tray is a unitary block of disposable, deformable material.

10. The method of claim 9 wherein said dental tray is made of expanded cellular polystyrene.

11. The method of claim 7 wherein said step of connecting said first end of said evacuation tube to a source of suction precedes said step of reinserting said apparatus into the mouth of the patient.

12. A method of applying fluoride to the teeth of a patient, comprising the steps of:

a) inserting into the mouth of the patient an apparatus comprising a dental tray, said dental tray having a top surface and a bottom surface, said top surface and said bottom surface being made of deformable material suitable for the making of an impression therein, said dental tray further having a side wall which extends from said top surface to said bottom surface, said side wall having a peripherally-extending groove, and said apparatus further comprising a frame mounted against said side wall, said frame having an evacuation tube formed therein, said evacuation tube having a first end adapted for communication with a source of suction, the remainder of said evacuation tube having a plurality of apertures spaced along the length thereof for aspirating materials therethrough, said remainder of said evacuation tube being disposed within said groove of said dental tray;

b) then, closing the mouth of the patient so that impressions of the upper and lower sets of teeth of the patient are simultaneously formed in said top surface and said bottom surface of said dental tray;

c) then, removing said apparatus from the mouth of the patient;

d) then, applying an appropriate amount of fluoride solution to the impressions in said top surface and said bottom surface of said dental tray;

e) connecting said first end of said evacuation tube to a source of suction;

f) reinserting said apparatus into the mouth of the patient, positioning said apparatus so that the impressions are aligned with the teeth of the patient;

g) then, closing the mouth of the patient so that the teeth fill the impressions and become completely immersed in the fluoride solution; and h) then, after waiting an effective amount of time, removing said apparatus from the mouth of the patient.

13. The method as claimed in claim 12, wherein said apparatus further comprises a first liner detachably mounted on said top surface and a second liner detachably mounted on said bottom surface, said method further comprising before applying the fluoride solution to the tray and after removing the apparatus from the mouth of the patient, the step of removing said first and second liners from said top and bottom surfaces, respectively.

* * * * *